US006295463B1

United States Patent
Stenzler

(12) United States Patent
(10) Patent No.: US 6,295,463 B1
(45) Date of Patent: Sep. 25, 2001

(54) SKIN PROTECTION MOUNT FOR TRANSCUTANEOUS SENSOR APPLICATION

(75) Inventor: Alex Stenzler, Orange, CA (US)

(73) Assignee: Sensormedics Corporation, Yorba Linda, CA (US)

( * ) Notice: Subject to any disclaimer, the term of this patent is extended or adjusted under 35 U.S.C. 154(b) by 0 days.

(21) Appl. No.: 09/477,190

(22) Filed: Jan. 4, 2000

(51) Int. Cl.$^7$ .................................................. A61B 5/04
(52) U.S. Cl. ......................... 600/391; 600/386; 607/152
(58) Field of Search .................................. 600/372, 386, 600/391, 392, 396; 607/152, 149; 602/41

(56) References Cited

U.S. PATENT DOCUMENTS

| | | | |
|---|---|---|---|
| 4,051,842 | * 10/1977 | Hazel et al. | 600/391 |
| 4,653,501 | * 3/1987 | Cartmell et al. | 128/640 |
| 4,773,424 | * 9/1988 | Inoue et al. | 128/641 |
| 4,945,911 | * 8/1990 | Cohen et al. | 128/640 |
| 4,947,853 | * 8/1990 | Hon | 128/662.03 |
| 5,848,966 | * 12/1998 | Gusakov et al. | 600/372 |
| 6,023,631 | * 2/2000 | Cartmell et al. | 600/372 |

* cited by examiner

Primary Examiner—Linda C. M. Dvorak
Assistant Examiner—David M. Ruddy
(74) Attorney, Agent, or Firm—Lyon & Lyon LLP

(57) ABSTRACT

A skin protection mount protects the skin surface of a subject from damage that can result from repeated attachment and detachment of transcutaneous sensors connected to the skin of a subject with adhesive. The skin protection mount preferably has a thickness of five mils or less, to provide increased flexibility and increase subject comfort. Preferably, the skin protection mount has adhesive on the side attached to the subject, and lacks adhesive on the opposite side in order to facilitate attachment to and detachment from a skin protection mount of a transcutaneous sensor having an adhesive zing with an adhesion surface. In a preferred embodiment, the mounting surface of the skin protection mount has a surface area larger than the adhesion surface to protect the subject's skin from the adhesion surface. The adhesive force between the skin protection mount and the patient is greater than the adhesive force between the skin protection mount and the adhesion surface of the adhesive ring.

24 Claims, 2 Drawing Sheets

SKIN PROTECTION MOUNT FOR TRANSCUTANEOUS SENSOR APPLICATION

BACKGROUND OF THE INVENTION

The field of invention is mounting transcutaneous sensors to a subject, and more specifically a skin protection mount for attachment to a subject between the subject's skin and a transcutaneous sensor.

Transcutaneous sensors are well-known noninvasive devices for measuring certain processes and properties of a subject. For example, a transcutaneous blood gas sensor allows for noninvasive measurement of the partial pressure of oxygen and carbon dioxide in the bloodstream by measuring the oxygen and carbon dioxide that permeate through the skin and into the sensor. A typical transcutaneous sensor has an electrode substantially resting against the skin that takes part in detecting the matters of interest. Generally, a layer of gel or solution is placed on the skin so that contact between the skin and the electrode takes places via that gel or solution. Transcutaneous sensors are usually attached to the skin with an adhesive ring having a sticky coating on both sides. One side of the adhesive ring is attached to the sensor, and the other half is attached to the skin. A hole in the center of the adhesive ring allows the electrode in the transcutaneous sensor to substantially touch the skin of the subject.

Commonly, the adhesive ring is attached to the sensor, and is removed from the skin with the sensor. Removal of the sensor occurs on a frequent basis. Transcutaneous blood gas sensors use a heated electrode, which can only be used in one place for a limited time before patient discomfort or an actual burn occurs; premature babies are particularly susceptible to such problems. Typically, such sensors must be removed from a given location on the subject after 2 hours of use in order to prevent discomfort or burns. A transcutaneous sensor may also be removed for placement on a different area of the patient, for replacement, or to allow patient movement without restriction by the sensor. As will be familiar to anyone who has removed an adhesive bandage, removing an adhesive item from the skin can be very irritating to quite painful, and can arouse significant apprehension, particularly in children. More importantly, when the adhesive ring is removed, it can pull up some of the skin layer with it. This can cause a problem with subjects having immature skin or skin disorders. For example, premature infants do not generally have a fully mature cutaneous layer. Yet, transcutaneous sensors must often be placed on premature infants to monitor and ensure their health. Thus, removal of those sensors can cause both pain and skin damage to premature infants.

To reduce skin damage, it is known to place plastic mounting rings on the subject's body at locations where transcutaneous sensing is desired. These plastic mounting rings are made of hard plastic and are thick enough, typically at least a millimeter, to be rigid. Such plastic mounting rings are placed on the subject once, and remain on the subject even when there is no sensor attached to them. A sensor can thus be attached to a plastic mounting ring, then detached from that plastic mounting ring and moved to a different plastic mounting ring, without the detaching process causing pain or skin damage. However, the plastic mounting rings are rigid, and can thus cause discomfort to the subject as he or she moves. They may be particularly uncomfortable for premature infants, for whom the plastic mounting rings are very large—typically about 0.75 inches in diameter—in comparison to their body size.

SUMMARY OF THE INVENTION

An object of the present invention is to provide a mounting surface for a transcutaneous sensor that protects a subject's skin from damage. Another object of the present invention is to provide a mounting surface for a transcutaneous sensor that is more comfortable for the subject than existing mounting surfaces. In one aspect of a preferred embodiment, a skin protection mount has a thickness of five mils or less, to provide greater flexibility and increase subject comfort. In another aspect of a preferred embodiment, the skin protection mount has adhesive on the side attached to the subject, and substantially lacks adhesive on the opposite side to facilitate attachment to and detachment from the skin protection mount of a transcutaneous sensor having an adhesive ring with an adhesion surface. In a further aspect of a preferred embodiment, the adhesive force between the skin protection mount and the patient is greater than the adhesive force between the skin protection mount and the adhesion surface of the adhesive ring. In another aspect of a preferred embodiment, the mounting surface of the skin protection mount has a surface area larger than the adhesion surface to protect the subject's skin from the adhesion surface. Other and further objects and advantages will appear hereinafter.

DETAILED DESCRIPTION OF THE PREFERRED EMBODIMENTS

Figure 1:
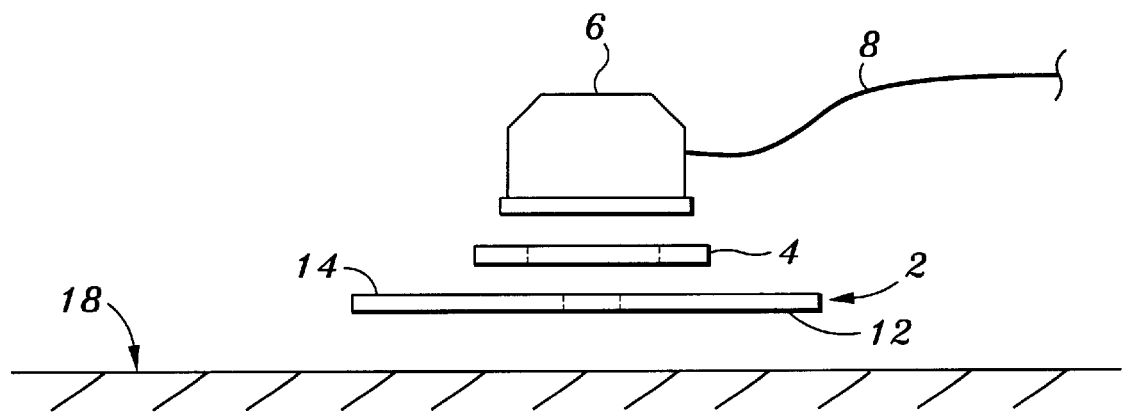
FIG. 1 is an exploded view of a preferred embodiment of a skin protection mount as used in conjunction with a sensor and a subject.

Referring to FIG. 1, a skin protection mount 2, an adhesive ring 4, and a transcutaneous sensor 6 can be seen. The transcutaneous sensor 6 may be a blood gas sensor or other type of sensor for detecting physiological information from a subject. Such information is typically transmitted to a computer or other monitoring device over a wire 8 or any other known form of communications transmission. Transcutaneous sensors 6 are well known in the art, and are readily available from several manufacturers; the present invention is not limited to use with any particular brand or model of transcutaneous sensor. One such device is the SensorMedics Microgram 7650 Transcutaneous Monitor.

Figure 2:
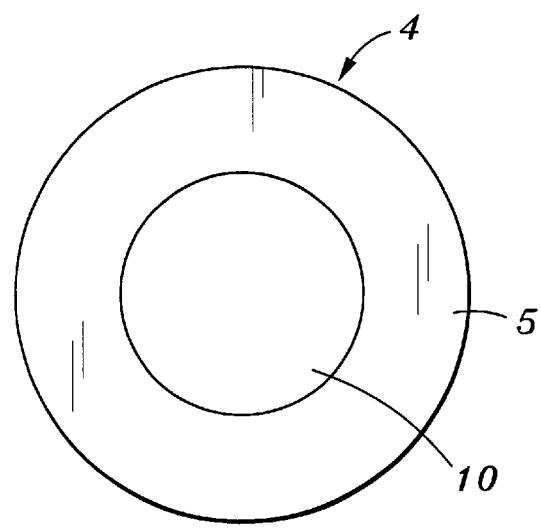
FIG. 2 is a bottom view of a preferred embodiment of an adhesive ring.
Figure 3:
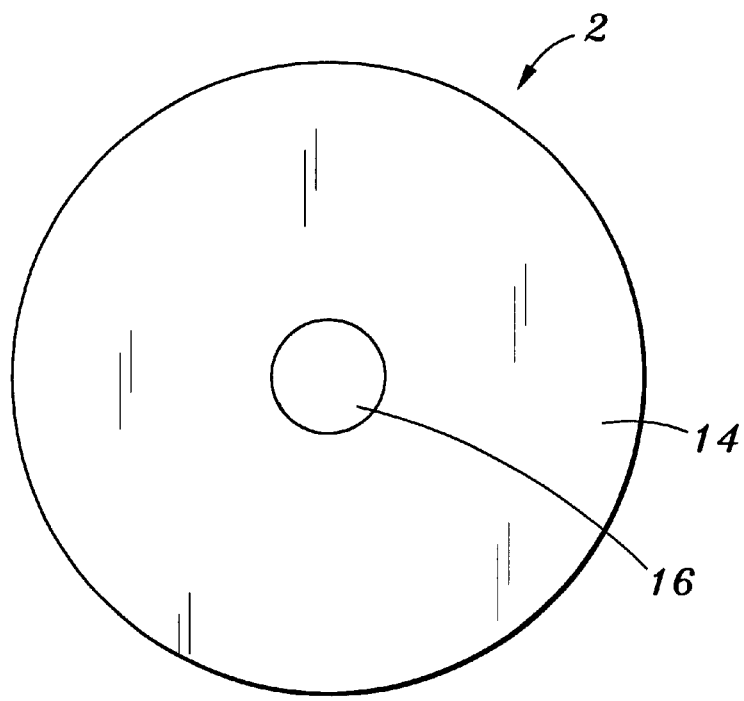
FIG. 3 is a top view of a preferred embodiment of a skin protection mount.

FIG. 1 shows the adhesive ring 4 as part of an exploded view. In a preferred embodiment, the adhesive ring 4 is substantially covered with adhesive on both sides. When the transcutaneous sensor 6 is in use, the sensor is attached to the adhesive ring 4 via that adhesive. Referring to FIG. 2, a bottom view of the adhesive ring 4 can be seen. A ring passage 10 extends through the adhesive ring 4. The adhesive ring 4 has an adhesion surface 5, which in the prior art is attached directly to the subject's skin 18. Referring back to FIG. 1, the skin protection mount 2 has an attachment surface 12, and a mounting surface 14 on the opposite side from the attachment surface 12. FIG. 3 shows a top view of the skin protection mount 2. A mount passage 16 extends through the skin protection mount 2.

In a preferred embodiment, the skin protection mount 2 is composed of polyethylene. However, the skin protection mount 2 can be made from other flexible, non-toxic materials capable of withstanding the stress of repetitive attachment and detachment of the adhesive ring 4 without substantially failure by tearing or otherwise.

In a preferred embodiment, the attachment surface 12 of the skin protection mount 2 is covered in whole or in part with an adhesive substance, in any manner or pattern that provides for secure attachment between the skin protection mount 2 and the subject's skin 18. Such adhesive substance maybe any nontoxic adhesive that is compatible with the subject's skin 18; the specific type of adhesive used is unimportant. In a preferred embodiment, the attachment surface 12 is substantially coated with acrylic co-polymer adhesive. In another preferred embodiment, the attachment surface 12 is substantially coated with acrylate adhesive. The attachment surface 12 of the skin protection mount 2 is then placed onto the subject's skin 18.

When placed on a patient, the skin protection mount 2 is meant to be permanently or non-removably attached to the patient. This means that the mount will remain attached to the skin when the sensor is detached from the patient. Of course, the mount can be removed from the patient whenever medical necessity, patient comfort or other need arises. Thus, in the preferred embodiment the skin protection mount 2 remains permanently or non-removably attached to the patient even when the sensor 6 is removed from or repositioned on the patient. Preferably, removal of the skin protection mount 2 only occurs primarily if the mount is somehow damaged, its adhesion to the skin becomes weakened, cleaning is needed, medical necessity requires removal, or further measurements are not required from the patient.

The mounting surface 14 is adapted to connect to the adhesive ring 4. The adhesion surface 5 of the adhesive ring 4 bears an adhesive substance with which the adhesive ring 4 is attached to the mounting surface. Preferably, that adhesive substance is acrylic co-polymer or acrylate. However, other adhesive substances capable of providing attachment between the adhesive ring 4 and the mounting surface 14 may be used if desired.

The adhesive force between the attachment surface 12 and the subject's skin 18 is greater than the adhesive force between the mounting surface 14 and the adhesive ring 4. The adhesive force is a function of the adhesive strength and the surface area over which it is applied. When it is desired to remove the sensor 6 and the adhesive ring 4 from the skin protection mount 2, a force slightly greater than the adhesive force between the adhesive ring 4 and the mounting surface 14 is applied to the adhesive ring 4. By providing for an adhesive force between the adhesive ring 4 and the mounting surface 14 that is less than the adhesive force between the attachment surface 12 and the subject's skin 18, the adhesive ring 4 may be easily removed from the skin protection mount 2, without inadvertently remaining attached to the skin protection mount 2 and detaching the skin protection mount 2 from the subject's skin 18 instead.

In a preferred embodiment, the same adhesive is used between the attachment surface 12 and the subject's skin 18 as used between the mounting surface 14 and the adhesive ring 4. Also in a preferred embodiment, the surface area of the interface between the attachment surface 12 and the subject's skin 18 is greater than the surface area of the interface between the adhesion surface 5 and the mounting surface 14. Thus, although the same adhesive is preferably used in both locations, the difference in surface area allows for greater adhesive force between the attachment surface 12 and the subject's skin 18 than between the adhesion surface 5 and the mounting surface 14. However, two different adhesives might be used with the stronger bonding adhesive between the skin and the mount.

Preferably, the mounting surface 14 is not substantially coated with adhesive. This is to avoid exposure of a sticky skin protection mount 2 to the patient's body after removal of the sensor 6 and the adhesive ring 4. For example, a premature baby may attempt to touch the mounting surface 14 after the sensor 6 is removed. However, the mounting surface 14 may be partially or completely covered with adhesive, as long as the resulting force between the adhesive ring 4 and the mounting surface 14 is less than the adhesive force between the attachment surface 12 and the subject's skin 18. While not required, a mounting surface cover (not shown) could be secured on the mounting surface 14 when the sensor 6 and adhesive ring 4 are removed, to protect the integrity of the mounting surface 14, especially if an adhesive covers the mounting surface 14 partially or completely. It will be understood that an amount of adhesive from the adhesion surface 5 may remain on the mounting surface 14 after removal of the adhesive ring 4 has been removed from the mounting surface 14. Such deposition of adhesive is expected, and does not constitute covering the mounting surface 14 with adhesive, completely or in part.

The skin protection mount 2 remains attached to the subject's skin 18 after the adhesive ring 4 has been detached from the mounting surface 14. As a result, the transcutaneous sensor 6 connected to the adhesive ring 4 can be changed out or moved as frequently as necessary without damage to the subject's skin 18 or discomfort to the subject, because the adhesive ring 4 is attaching to and detaching from the skin protection mount 2 rather than the subject's skin 18.

The thickness of the skin protection mount 2 is a tradeoff between the limitations of the transcutaneous sensor 6 and the need for patient comfort. The comfort of a patient wearing the skin protection mount 2 increases as the skin protection mount 2 grows thinner. A thinner skin protection mount 2 is more capable of flexing with the skin 18, and is less likely to cause discomfort when a subject rests or lies on it, or otherwise applies pressure to it. A countervailing consideration is the need for the skin protection mount 2 to be strong enough to withstand repeated attachment and detachment of the adhesive ring 4 without substantially tearing.

Another countervailing consideration is the operation of the transcutaneous sensor 6. In order to sense blood gas permeating through the skin 18, the transcutaneous sensor 6 typically includes an electrode (not shown) which must substantially contact the subject's skin 18 in order to perform properly. Such contact is typically through a gel or solution placed on the subject's skin 18. In known transcutaneous sensors 6, that electrode will not reliably contact the subject's skin 18 if the transcutaneous sensor 6 is located more than substantially 8 mils from the skin. The adhesive ring 4 is typically 1–3 mils thick.

Thus, in a preferred embodiment for use with such a typical adhesive ring 4, the skin protection mount 2 is five mils thick or less, to allow the electrode from the transcutaneous sensor 6 to pass through the mount passage 16 and substantially contact the subject's skin 18. It will be noted that an increase in thickness of the adhesive ring 4 used may correspondingly decrease the thickness of the skin protection mount 2 in order to ensure that the electrode (not shown) in the transcutaneous sensor 6 substantially touches the subject's skin 18. A skin protection mount 2 thickness of five mils or less is also desirable from a patient comfort standpoint.

Preferably, the skin protection mount is substantially three mils thick. However, the skin protection mount 2 may be thinner than three mils, and made of any nontoxic thin film, so long as the skin protection mount 2 is mechanically able to withstand repeated attachment of the adhesive ring 4 to and removal of the adhesive ring 4 from the mounting surface 14 without substantially tearing.

It should also be recognized that advances in sensor technology in the future might well allow the transcutaneous sensor 6 to be placed more than 8 mils from the skin and still function effectively. Thus, within the scope of this invention, is the concept of providing a skin protection mount 2 up to substantially 25 mils thick for use with such advanced transcutaneous sensors 6. A skin protection mount 2 having a thickness of substantially 25 mils would still provide for flexibility and comfort, and would possess the same advantages and operate in the same manner as disclosed above.

When the transcutaneous sensor 6 is attached to the skin protection mount 2, the ring passage 10 and the mount passage 16 are sized and aligned such that the electrode (not shown) of the transcutaneous sensor 6 has adequate space to extend through both the ring passage 10 and the mount passage 16 and substantially touch the skin of the subject. Other than this consideration, the actual or relative size of the ring passage 10 and the mount passage 16 is not critical for obtaining the desired information. Nevertheless, the size of the mount passage 16 is constrained by the function of the skin protection mount 2. The mount passage 16 preferably encompasses a smaller area than the ring passage 10, to minimize the possibility of the adhesive ring 4 being misplaced on the skin protection mount 2 in such a way as to contact the subject's skin 18 through the mount passage 16. If the mount passage 16 is too large, then the adhesive ring 4 will simply pass through the mount passage 16 and attach directly to the skin of the subject; such attachment is what the skin protection mount 2 is intended to minimize. If the mount passage 16 is too small, the electrode in the transcutaneous sensor 6 will not be able to extend through and substantially touch the skin of the subject. Any size and shape of mount passage 16 that allows the electrode in the transcutaneous sensor 6 to extend through and substantially touch the skin of the subject, while minimizing contact between the adhesive ring 4 and the skin of the subject, is preferably used.

Additionally, the preferred size of the mount passage 16 will depend on the model of transcutaneous sensor 6 used, particularly the size of electrode utilized by the transcutaneous sensor 6. In a preferred embodiment, the skin protection mount 2 is substantially circular with a diameter of substantially 32 millimeters, and the mount passage 16 is substantially circular with a diameter of substantially 11 millimeters.

In a preferred embodiment, the surface area of the mounting surface 14 is larger than the surface area of the adhesion surface 5 of the adhesive ring 4 in order to minimize or prevent contact between the adhesive ring 4 and the subject's skin 18. FIG. 1 shows the skin protection mount 2 substantially larger than the adhesive ring 4. The skin protection mount 2 is also shaped to minimize or prevent contact between the adhesive ring 4 and the subject's skin 18. In this way, different sizes and shapes of skin protection mount 2 are contemplated for use in conjunction with different sizes and shapes of adhesive ring 4.

Figure 4:
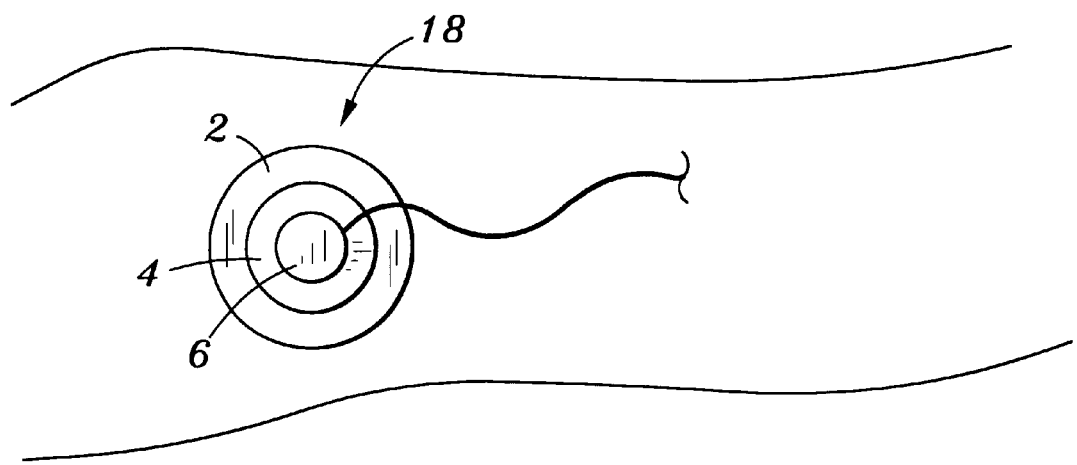
FIG. 4 is a top view of a preferred embodiment of a skin protection mount as used in conjunction with a sensor and a subject.

The majority of adhesive rings 4 in the market are substantially circular, and the majority of transcutaneous sensors 6 are substantially circular as viewed from the top. Thus, in a preferred embodiment, the skin protection mount 2 takes the form of a substantially circular disk, with a diameter larger than that of the adhesive ring 4, where the mount passage 16 is located at substantially the center of the skin protection mount 2. As seen in FIG. 4, the adhesive ring 4 is preferably attached to the skin protection mount 2 such that the two are substantially centered, allowing for simple alignment of the two. As a result, the ring passage 10 and the mount passage 16 are substantially aligned, thereby substantially preventing the adhesive ring 4 from contacting the subject's skin 18.

In an alternate embodiment, the surface area of the mounting surface 14 is substantially the same as the surface area of the adhesion surface 5 of the adhesive ring 4, and the skin protection mount 2 has a shape adapted to substantially match the shape of the adhesive ring 4 in order to minimize contact between the adhesive ring 4 and the subject's skin 18. More care must be taken with the application of the adhesive ring 4 in this alternate embodiment, as misalignment will typically result in greater contact between the adhesive ring 4 and the subject's skin 18 than in the preferred embodiment.

A preferred skin protection mount for sensor application and many of its attendant advantages have thus been disclosed. It will be apparent, however, that various changes may be made in the materials and components without departing from the spirit and scope of the invention, the materials and components hereinbefore described being merely preferred or exemplary embodiments thereof. For example, the sensor 6 and the adhesive ring 4 might be constructed as a single unit, wherein the adhesive ring 4 may be reused for multiple applications of the sensor 6. As another example, a ring cap may be provided for the adhesive ring 4 to protect the sensor and ring integrity before or after the adhesive ring 4 is attached to the skin protection mount 2. Therefore, the invention is not to be restricted or limited except in accordance with the following claims and their legal equivalents.

What is claimed is:

1. An apparatus for protecting the skin of a subject comprising:
   an adhesive ring having a ring passage therethrough and an adhesion surface; and
   a flexible skin protection mount permanently attached to a patient, having an attachment surface at the interface between the flexible skin protection mount and the skin of the patient bearing an adhesive, an opposed mounting surface onto which the adhesion surface of the adhesive ring adheres, and a mount passage extending therethrough and encompassing an area smaller than the area encompassed by the ring passage, said mounting surface having a larger surface area than the adhesion surface of the adhesive ring.

2. The apparatus of claim 1, wherein the adhesive force between said attachment surface and the patient is greater than the adhesive force between said mounting surface and the adhesion surface of the adhesive ring.

3. The apparatus of claim 1, wherein said adhesion surface bears adhesive and said mounting surface is substantially free of adhesive.

4. The apparatus of claim 1, wherein said skin protection mount is less than or substantially equal to five mils thick.

5. The apparatus of claim 1, wherein said skin protection mount is composed of polyethylene.

6. The apparatus of claim 1, wherein said adhesive on said attachment surface is acrylic co-polymer.

7. The apparatus of claim 1, wherein said adhesive on said attachment surface is acrylate.

8. The apparatus of claim 1, further comprising a ring cap secured to the adhesive ring when the adhesive ring is not attached to said mounting surface.

9. The apparatus of claim 1, wherein the adhesive ring is part of a unitary sensor assembly.

10. An apparatus for protecting the skin of a subject comprising:

an adhesive ring having a ring passage therethrough and an adhesion surface;

a flexible skin protection mount permanently attached to a patient, having an attachment surface at the interface between the flexible skin protection mount and the skin of the patient bearing an adhesive, an opposed mounting surface onto which the adhesion surface of the adhesive ring adheres, and a mount passage extending therethrough and encompassing an area smaller than the area encompassed by the ring passage, said mounting surface having a surface area and shape substantially the same as the surface area and shape of the adhesion surface of the adhesive ring; and wherein the adhesive force between said attachment surface and the patient is greater than the adhesive force between said mounting surface and the adhesion surface of the adhesive ring.

11. The apparatus of claim 10, wherein said adhesion surface bears adhesive and said mounting surface is substantially free of adhesive.

12. The apparatus of claim 10, wherein said skin protection mount is less than or substantially equal to five mils thick.

13. The apparatus of claim 10, wherein said skin protection mount is composed of polyethylene.

14. The apparatus of claim 10, wherein said adhesive on said attachment surface is acrylic co-polymer.

15. The apparatus of claim 10, wherein said adhesive on said attachment surface is acrylate.

16. The apparatus of claim 10, further comprising a ring cap secured to the adhesive ring when the adhesive ring is not attached to said mounting surface.

17. The apparatus of claim 10, wherein the adhesive ring is part of a unitary sensor assembly.

18. A skin protection mount for use with a transcutaneous sensor comprising:

a transcutaneous sensor having an electrode;

an adhesive ring having a ring passage between first and second sides thereof, the transcutaneous sensor being attached to the first side of the adhesive ring with an adhesive, wherein the electrode of the transcutaneous sensor passes through the ring passage;

a skin protection mount having a mount passage extending between an attachment surface for permanently attaching the skin protection mount to the skin of the patient using an adhesive and an opposing mounting surface for releasably engaging with the second side of the adhesive ring using an adhesive; and wherein the transcutaneous sensor and adhesive ring are releasably engagable with the opposing mounting surface of the skin protection mount such that the electrode of the transcutaneous sensor passes through the mount passage to substantially contact the patient's skin when the transcutaneous sensor and adhesive ring are engaged with the surface protection mount and such that the adhesive force between the attachment surface of the skin protection mount and the skin of the patient is greater than the adhesive force between the opposing mounting surface of the skin protection mount and the second side of the adhesive ring.

19. The apparatus of claim 18, wherein the adhesive ring has a thickness between 1 and 3 mils.

20. The apparatus of claim 19, wherein the skin protection mount has a thickness of five mils or less.

21. The apparatus of claim 18, wherein the mount passage is smaller than the ring passage.

22. The apparatus of claim 18, wherein the surface area of the interface between the skin protection mount and the patient's skin is greater than the surface area of the interface between the adhesive ring and the skin protection mount.

23. The apparatus of claim 18, wherein a stronger adhesive is used between the interface between the skin protection mount and the patient's skin than the adhesive used between the interface between the adhesive ring and the skin protection mount.

24. A method of protecting the skin of a patient from a transcutaneous sensor having an electrode comprising the steps of:

adhering the transcutaneous sensor to an adhesive ring with an adhesive, the adhesive ring having a ring passage therethrough for passage of the electrode;

adhering to the skin a non-removable, flexible skin protection mount with an adhesive, the non-removable, flexible skin protection mount having a mount passage therethrough for passage of the electrode; and adhering the transcutaneous sensor and adhesive ring to the non-removable, flexible skin protection mount with an adhesive, wherein the adhesive force between the non-removable, flexible skin protection mount and the patient's skin is greater than the adhesive force between the non-removable, flexible skin protection mount and the adhesive ring and wherein the electrode from the transcutaneous sensor passes through the ring passage and the mount passage to substantially contact the patient's skin.

* * * * *

UNITED STATES PATENT AND TRADEMARK OFFICE
CERTIFICATE OF CORRECTION

PATENT NO.    : 6,295,463 B1
DATED         : September 25, 2001
INVENTOR(S)   : Stenzler It is certified that error appears in the above-identified patent and that said Letters Patent is hereby corrected as shown below:

<u>Title page,</u>
Item [57], ABSTRACT,
Line 11, change "zing" to -- ring --.

<u>Column 1,</u>
Line 33, change "bum" to -- burn --.

<u>Column 2,</u>
Line 53, change "Microgram" to -- Microgas --.

Signed and Sealed this

Eleventh Day of June, 2002

Attest:

Attesting Officer

JAMES E. ROGAN
*Director of the United States Patent and Trademark Office*